US011744756B2

(12) United States Patent
Salloum

(10) Patent No.: US 11,744,756 B2
(45) Date of Patent: Sep. 5, 2023

(54) SYSTEM AND APPARATUS FOR PATIENT POSITIONING AND METHODS OF USE

(71) Applicant: Gabriel Salloum, Mandeville, LA (US)

(72) Inventor: Gabriel Salloum, Mandeville, LA (US)

(*) Notice: Subject to any disclaimer, the term of this patent is extended or adjusted under 35 U.S.C. 154(b) by 274 days.

(21) Appl. No.: 17/324,792

(22) Filed: May 19, 2021

(65) Prior Publication Data

US 2021/0361510 A1 Nov. 25, 2021

Related U.S. Application Data

(60) Provisional application No. 63/026,747, filed on May 19, 2020.

(51) Int. Cl.
*A61G 13/12* (2006.01)
*A61F 5/37* (2006.01)
*A61G 13/04* (2006.01)

(52) U.S. Cl.
CPC .......... *A61G 13/121* (2013.01); *A61F 5/3707* (2013.01); *A61G 13/04* (2013.01); *A61G 13/123* (2013.01)

(58) Field of Classification Search
CPC .......... A61H 2001/0203; A61G 13/121; A61G 13/04; A61G 13/123
See application file for complete search history.

(56) References Cited

U.S. PATENT DOCUMENTS

| 4,244,358 | A | * | 1/1981 | Pyers | A61G 7/001 5/607 |
| 7,328,469 | B2 | * | 2/2008 | Vrzalik | A61G 13/00 5/607 |
| 9,339,430 | B2 | | 5/2016 | Jackson | |
| 10,426,684 | B2 | * | 10/2019 | Dubois | A61G 13/0054 |
| 10,751,240 | B2 | * | 8/2020 | Lim | A61G 7/015 |
| 2017/0181908 | A1 | * | 6/2017 | Jackson | A61G 7/005 |
| 2019/0209409 | A1 | * | 7/2019 | Jackson | A61G 13/04 |
| 2021/0085550 | A1 | * | 3/2021 | Lim | A61G 13/08 |

* cited by examiner

*Primary Examiner* — David R Hare
*Assistant Examiner* — Adam C Ortiz
(74) *Attorney, Agent, or Firm* — Carlton Fields, PA; Eleanor M. Yost

(57) ABSTRACT

A patient positioning system and methods therefore including apparatuses having a base frame assembly operable to position a patient, adjustably-attached attached to a gimbal, wherein the gimbal is rotatable about two or more axes relative to the base frame assembly.

23 Claims, 12 Drawing Sheets

SYSTEM AND APPARATUS FOR PATIENT POSITIONING AND METHODS OF USE

CROSS RELATED APPLICATIONS

This application claims priority to U.S. Provisional Application No. 63/026,747, which was filed on May 19, 2020, and which is hereby incorporated by reference in its entirety.

FIELD OF THE INVENTION

The present invention relates to a system and apparatus for patient positioning, including vertical, lateral, and prone positioning, and patient repositioning, including perioperative and intraoperative repositioning.

The present invention also relates to methods of use of the system and apparatus for patient positioning and methods of patient positioning.

BACKGROUND

Current patient support systems do not adequately allow healthcare providers to selectively position patients in a variety of positions. This is limiting to healthcare providers in their ability to perform certain clinical procedures and offer patients certain treatments. During surgery, for example, a patient may be required to be moved into many surgical positions intraoperatively. Standard operating room tables do not permit such patient re-positioning, so patients need to be positioned manually, often requiring multiple staff members. This takes time, and significant manpower, and delays the procedure. The inventions described herein address these issues by permitting healthcare providers to selectively position the patient, even intraoperatively. As such, in the example described above, the surgeon is able to achieve surgical goals easier and faster. Additionally, cost is decreased by reducing the manpower necessary for positioning, and patient safety is improved by significantly decreasing overall operative time and the risk to the patient's airway and joints by manual positioning.

Several different types of patient positions may be used in medical procedures, including but not limited to: (1) supine, or the position of the body at rest, making it the most common posture for surgery; (2) Trendelenburg, a variation of the supine position where the upper torso is lowered and the feet raised, allowing for optimal visualization of the pelvic organs during laparoscopy and lower abdominal procedures; (3) Reverse Trendelenburg, more commonly known as the head-up and feet-down position, which is often used in head and neck procedures; (4) prone, where the patient lies flat on their stomach and their head is turned to the side, which is most commonly used for cervical spine, back, and rectal area procedures; (5) lithotomy, where the patient is in supine position and their legs are raised and abducted and feet placed in stirrups; and (6) sitting, or Fowler's position, where the patient is sitting at a 90 degree angle and the knees are slightly flexed and the feet are placed against a padded foot board, which is frequently used during neurosurgery; and (7) lateral, where the patient is positioned on the non-operative side to that surgery can be performed on the hip, chest, or kidney.

In some procedures two or more, or partial, or modified versions, of such positions may be necessary. Current apparatuses for patient positioning do not adequately allow for perioperative and intraoperative repositioning of a patient who is undergoing a clinical procedure. Changing a patient's positioning before, during, and after a procedure is a complex, time-intensive, and effort-intensive process. It can cause significant setback, and it can require participation by many healthcare providers or apparatuses. This is especially true in situations where patients cannot assist in moving themselves, such as patients with limited mobility or responsiveness. This can be due to, for example, trauma or other injury, being under anesthesia, such as during surgery, or the existence of one or more health conditions.

In procedures that require a sterile operating field, it is especially challenging to reposition a patient intraoperatively while maintaining the sterility of the operating field. This necessitates operative planning around repositioning, and/or repositioning requires re-sterilization, and/or repositioning is simply not a safe option during certain patient states. All these factors can cause interruption and delay.

Conventional operating tables generally include structure that permits tilting or rotation of a patient support surface about a longitudinal axis. But such designs typically employ either a massive base to counterbalance the extended support member, or a large overhead frame structure to provide support from above. The enlarged base members associated with such designs are problematic in that they can and do obstruct the movement of C-arm and O-arm mobile fluoroscopic imaging devices and other equipment. Surgical tables with overhead frame structures are bulky and may require the use of dedicated operating rooms, since in some cases they cannot be moved easily out of the way. Neither of these designs is easily portable or storable.

U.S. Pat. No. 9,339,430 describes a patient support apparatus for supporting a patient in a prone position during a surgical procedure, including a patient support structure incorporating an open fixed frame suspended above a floor and a pair of spaced opposed radially sliding joints cooperating with the frame, each joint including a virtual pivot point and an arc of motion spaced from the pivot point, the joints being movable along the arc providing a pivot-shift mechanism for a pair of pelvic pads attached to the joints being adapted to rotate a patient support structure 180 degrees for inverted orientation. It does not disclose a system for patient positioning or repositioning, vertically, laterally, or prone, perioperative or intraoperative repositioning, or repositioning while maintaining sterility of an operating field.

There remains a need for a patient support system that permits adjustable positioning and repositioning a patient's head and upper body, lower body and limbs in individual planes while permitting tilting, rotating, bending and other manipulations as well as full and free access to the patient by medical personnel and equipment.

SUMMARY OF THE INVENTION

Certain embodiments of the disclosed invention may comprise apparatuses for patient positioning, including vertically, laterally, and prone positioning, and patient repositioning, including perioperative and intraoperative repositioning.

In one form, an embodiment of the invention comprises a patient positioning system, having a base frame assembly operable to position a patient, adjustably-attached attached to a gimbal, wherein the gimbal is rotatable about two or more axes relative to the base frame assembly.

In another form, an embodiment of the invention comprises a patient positioning apparatus having a longitudinal axis, a lateral axis, and a vertical axis, where each axis is perpendicular to the other axes. The apparatus further comprises a base frame assembly operable to support a patient and a longitudinal base bar, wherein the longitudinal base bar extends along the longitudinal axis and is located approximately at a bottom of the vertical axis; a head base, wherein the head base extends along the lateral axis and is located approximately at a first end of the longitudinal axis and the bottom of the vertical axis; a foot base, wherein the foot base extends along the lateral axis and is located approximately at a second end of the longitudinal axis opposite the first end of the longitudinal axis and the bottom of the vertical axis; a left hip base, wherein the left hip base extends along the lateral axis and is located approximately at the bottom of the vertical axis and between the first end and the second ends of the longitudinal axis; a right hip base, wherein the right hip base extends along the lateral axis and is located approximately at the bottom of the vertical axis and between the first end and the second end of the longitudinal axis; a head support, wherein the head support extends along the vertical axis and is located approximately at the first end of the longitudinal axis; a foot support, wherein the foot support extends along the vertical axis and is located approximately at the second end of the longitudinal axis; a left hip support, wherein the left hip support extends along the vertical axis and is located between the first and the second ends of the longitudinal axis; and a right hip support, wherein the right hip support extends along the vertical axis and is located a between the first and the second ends of the longitudinal axis. The apparatus may further include a gimbal, comprising a head tube or shaft having a head tube head/top and a head tube foot/bottom, wherein the head tube head further comprises a roll member, a head pad, and a hip tube, that further includes a hip tube left and a hip tube right, wherein the hip tube right further comprises a pitch member. The gimbal may further include a foot tube/shaft that includes a foot tube head/top and a foot tube foot/bottom and a foot assembly where the head tube head is attached to the head support, the foot tube foot is attached to the foot support, the hip tube left is attached to the left hip support, the hip tube right is attached to the right hip support, the gimbal is rotatable about the longitudinal axis, the roll member controls the gimbal's rotation about the longitudinal axis, the gimbal is rotatable about the lateral axis, and the pitch member controls the gimbal's rotation about the lateral axis.

In yet another form, an embodiment of the invention comprises a method of patient positioning on an apparatus comprising a frame and a gimbal, wherein the gimbal is attached to the frame at two or more attachment points, the gimbal is operable of rotation about two or more axes relative to the frame, one axis of rotation contains one or more of the attachment points, and each of the other one or more axes of rotation contain one or more of the other attachment points. The method comprises the steps of selecting an axis of rotation in order to position the patient in a desired location or position, detaching the gimbal from the frame at the one or more attachment points not in the axis of desired rotation; rotating the gimbal relative to the frame about the desired axis of rotation; and attaching the gimbal to the frame at the one or more attachment points in the axis of desired rotation.

Further embodiments of the disclosed invention may comprise methods of apparatus positioning.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

In the following description, details are set forth for purpose of explanation. The embodiments and descriptions disclosed herein are intended, therefore, to be illustrative only and not limiting. Similarly, where examples are used herein, the examples are not intended to be limiting unless the context in which the example is used clearly indicates otherwise. Accordingly. "for example" or "e.g." should be read as "for example, and without limitation," unless the context indicates that limitation to the given example(s) is intended. The meaning of certain terms may be defined herein or will otherwise be apparent to those of ordinary skill as the ordinary meanings used in the art. Words importing the singular include the plural and vice versa unless the context clearly indicates otherwise. Words importing gender include the masculine, feminine, and neuter genders unless the context clearly indicates otherwise.

Use of measurements and units herein are approximate and not meant to be exact. Accordingly, language in the form of "n units," where n is any numerical value and units is any unit of measurement, should be read as "about n units," "approximately n units," "around n units," or "roughly n units."

As used herein, the terms "affix" and "attach" and their grammatical derivatives can mean any temporary or permanent adhesive means, mechanical means, insertion, incorporation, or integration, etc., or a combination thereof. Adhesive means can comprise welding, wood glue, glue, hot glue, epoxy, resin poly(methylacrylate), or polyurethane, etc., or a combination thereof. Mechanical means can comprise hooks, pins, screws, nuts, bolts, or nails, etc., or a combination thereof. Attached or attaching, or affixed or affixing, in this context, and in reference to the embodiments described herein, include permanently, temporarily or removably, and adjustably-attaching and affixing, by any of a variety of the aforementioned and other means, as will be readily apparent to those of ordinary skill in the art.

As used herein, the term "apparatus" can mean structure, system, device, product, assembly, or machine. Embodiments of apparatuses disclosed herein are intended to include the meanings conveyed by the terms surgical table, surgical chair, operating table, operating chair, procedural table, or procedural chair. Where the term "tube" is disclosed, it is intended to include shafts, rotational tubes, rotational shafts, and the like.

Disclosed herein are apparatuses for patient positioning. In certain embodiments, an apparatus for patient positioning comprises a base frame and a gimbal wherein the gimbal is adjustably-attached to the base frame, the gimbal is operable of rotating about two or more axes relative to the frame, and the gimbal is adapted to support an occupant. A gimbal is a pivoted support that permits rotation of an object about an axis.

Figure 1:
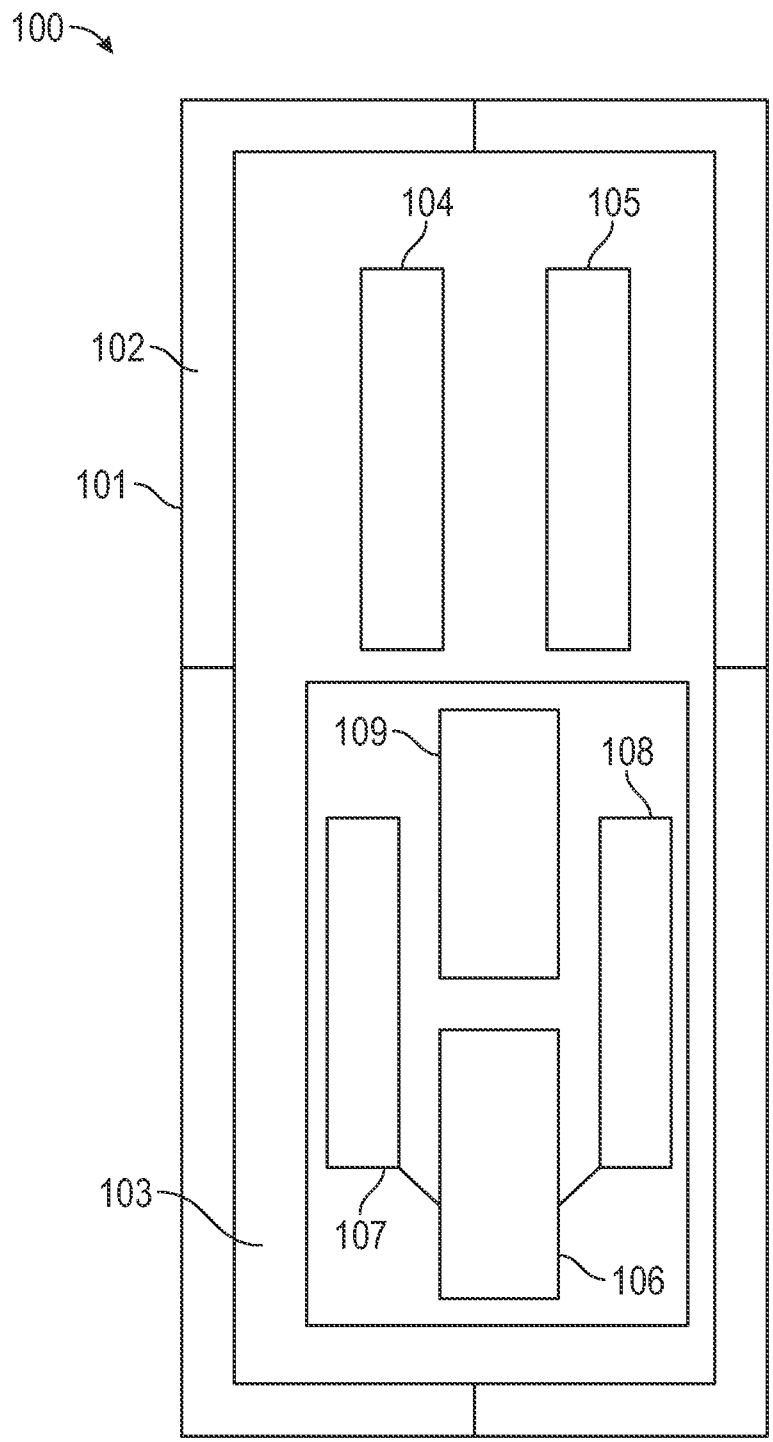
FIG. 1 is a schematic view of an embodiment of an apparatus for patient positioning.

Referring to FIG. 1, a schematic illustration is shown of an embodiment of an apparatus for patient positioning. Apparatus 100 comprises a base 101 and gimbal 102, wherein gimbal 102 further comprises flexion assembly 103 and two lower extremity assemblies 104 and 105, and head and shoulders assembly 106, arm assemblies 107 and 108, and lumbar assembly 109. There assemblies are further detailed in herein.

Figure 2A:
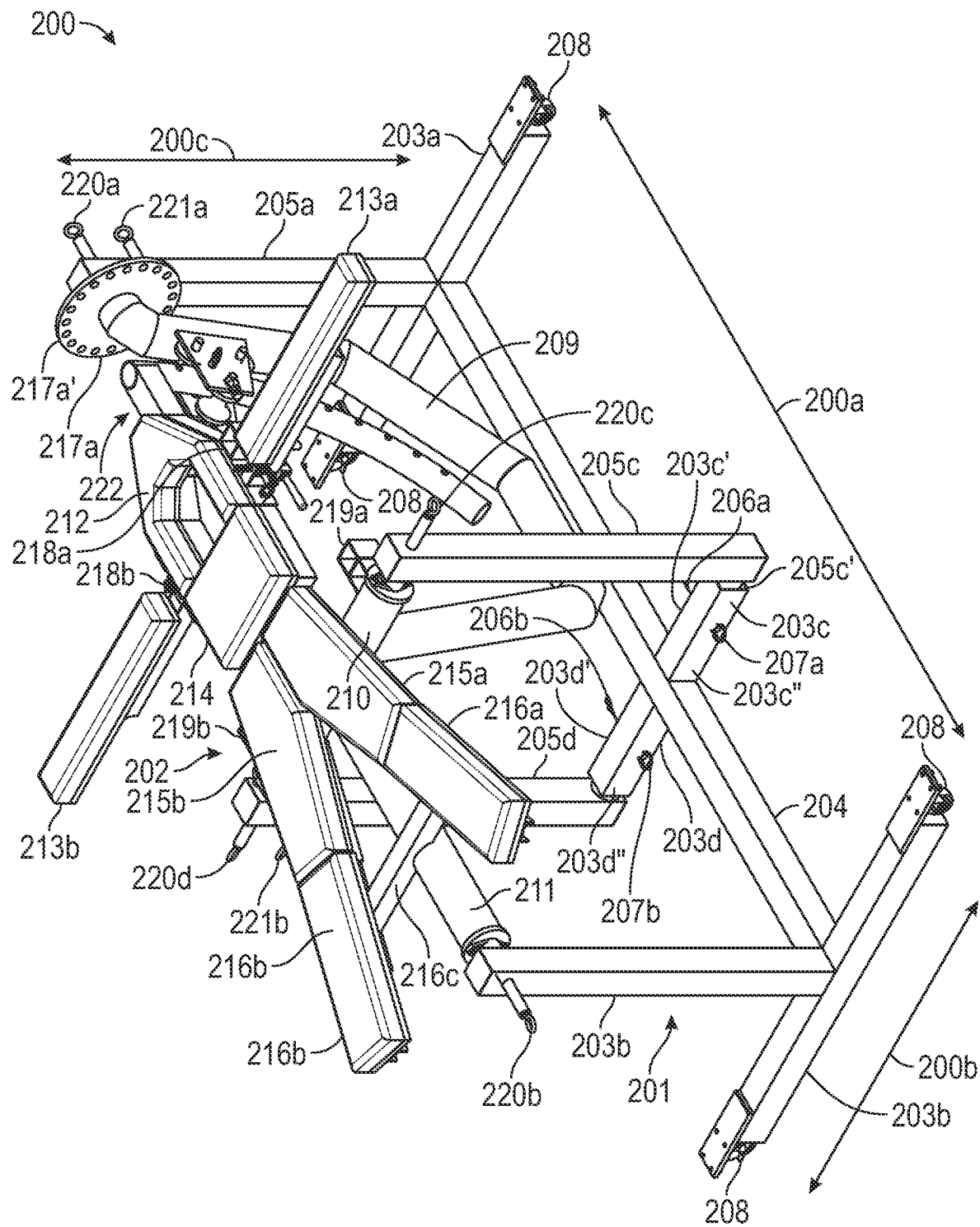
FIG. 2A is an orthogonal view of an embodiment of an apparatus for patient positioning illustrating a supine positioning configuration.

FIG. 2A depicts an orthogonal view of an embodiment of an apparatus for patient positioning 200. Apparatus 200 has longitudinal axis 200a that extends lengthwise along the apparatus head-to-foot, a lateral axis 200b, and a vertical axis 200c that extends up from the floor. Each of the axes are perpendicular to the others. Longitudinal axis 200a is functionally equivalent to a roll axis, lateral axis 200b a pitch axis and vertical axis 200c a yaw axis.

Apparatus 200 comprises base frame assembly 201 and gimbal assembly 202. Base frame assembly 201 comprises head base 203a, foot base 203b, left hip base 203c, right hip base 203d, longitudinal base bar 204, head support 205a, foot support 205b, left hip support 205c, and right hip support 205d. Longitudinal base bar 204 is oriented along longitudinal axis 200a; head base 203a, foot base 203b, left hip base 203c, and right hip base 203d are oriented along lateral axis 200b; and head support 205a, foot support 205b, left hip support 205c, and right hip support 205d are oriented along vertical axis 200c. The longitudinal axis head of longitudinal base bar 204 is affixed approximately to midpoint of head base 203a (along the lateral axis) and the bottom of head support 205a (along the vertical axis). The longitudinal axis foot of longitudinal base bar 204 is affixed approximately to the midpoint of foot base 203b (along the lateral axis) and the bottom of foot support 205b (along the vertical axis).

Approximately at the midpoint of longitudinal base bar 204 along the longitudinal axis, longitudinal base bar 204 is affixed approximately to the right end of left hip base 203c and the left end of right hip base 203d. Left hip support 205c is adjustably attached to left hip base 203c and right hip support 205d is adjustably attached to right hip base 203d. As shown in FIG. 2A, this is accomplished via a nut-and-bolt mechanism, but other \attachment means will be readily apparent to those of ordinary skill in the art.

In apparatus 200, left hip base 203c is hollow and further comprises holes 203c' and 203c'' at the head and foot along the longitudinal axis, respectively, of left hip base 203c, approximately at midpoint of the lateral axis and midpoint of left hip base 203c along the vertical axis. Right hip base 203d is hollow and further comprises holes 203d' and 203d'' at the head and foot along the longitudinal axis, respectively, of right hip base 203d, approximately at the midpoint of right hip base 203d along the lateral and vertical axes. Left hip support 205c further comprises peg 205c' protruding rightward from bottom of left hip support 205c along the vertical axis; and right hip support 205d further comprises peg 205d' protruding leftward from bottom of right hip support 205d along the vertical axis. Pegs 205c', 205d' each further comprise holes such that the holes of peg 205c' align with holes 203c', 203c'' when peg 205c' is inserted into the hollow space of left hip base 203c, and such that the holes of peg 205d' align with holes 203d', 203d'' when peg 205d' is inserted into the hollow space of right hip base 203d. Left hip support 205c attaches to left hip base 203c when peg 205c' inserts into the hollow space of left hip base 203c, and when screw 206a passes through hole 203c', the holes of peg 205c', and hole 203c'', and bolt 207a secures screw 206a in place. Similarly, right hip support 205d attaches to right hip base 203d when peg 205d' inserts into the hollow space of right hip base 203d, and when screw 206b passes through hole 203d', the holes of peg 205d', and hole 203d'', and bolt 207b secures screw 206b in place.

In some embodiments, head base 203a and foot base 203b further comprise wheel assemblies 208, wherein wheel assemblies 208 are attached approximately to the left and right ends of head base 203a and foot base 203b along the lateral axis, and are used to, for example, maneuver the apparatus.

Gimbal assembly 202 comprises head tube 209, hip tube 210, foot tube 211, head pad 212, and foot pad assembly 216, and may further comprise left arm pad 213a, right arm pad 213b, lumbar pad 214, left thigh pad 215a, and right thigh pad 215b.

Head tube 209 is roughly in the shape of the letter "n", and further comprises roll member 217a, which further comprises holes 217a'. Hip tube 210 is oriented lengthwise along lateral axis 200b, and further comprises pitch member 217b (not seen in FIG. 2A) at the lateral axis right end of hip tube 210, and further comprises hip cage receivers 219a, 219b approximately left and right ends, respectively, of hip tube 210; and foot tube 211 is oriented lengthwise along longitudinal axis 200a.

Head tube 209 is attached to the top of head support 205a via pin 220a and roll pin 221a; the foot of head tube 209 is attached approximately to the midpoint of hip tube 210 along the lateral axis. Left end of hip tube 210 is attached to the top of left hip support 205c via pin 220c; the right end of hip tube 210 is attached to the top of right hip support 205d via pin 220d and flexion pin 221b.

The head of foot tube 211 is attached to the midpoint of hip tube 210 and the foot of foot tube 211 is attached approximately to the top of foot support 205b along the vertical axis via pin 220b.

Head pad 212 is attached to head tube 209 via flexion assembly 222. Head pad 212 further comprises shoulder cage receivers 218a and 218b along the lateral axis left and right sides, respectively, of head pad 212. Left arm pad 213a attaches near the left side of head pad 212. Right arm pad 213b attaches near the right side of head pad 212. Lumbar pad 214 attaches near the foot of head pad 212 along the longitudinal axis.

Foot pad assembly 216 comprises left foot pad 216a, right foot pad 216b, and center bar 216c, wherein center bar 216c is oriented in lateral axis 200b, left foot pad 216a is affixed approximately to the left end of center bar 216c, and right foot pad 216b is affixed approximately to right end of center bar 216c. Foot pad assembly 216 is affixed to foot tube 211 at approximately midpoint of center bar 216c along the lateral axis and midpoint of foot tube 211 along the longitudinal axis. Left thigh pad 215a attaches to left foot pad 216a and right thigh pad 215b attaches to right foot pad 216b.

Figure 2B:
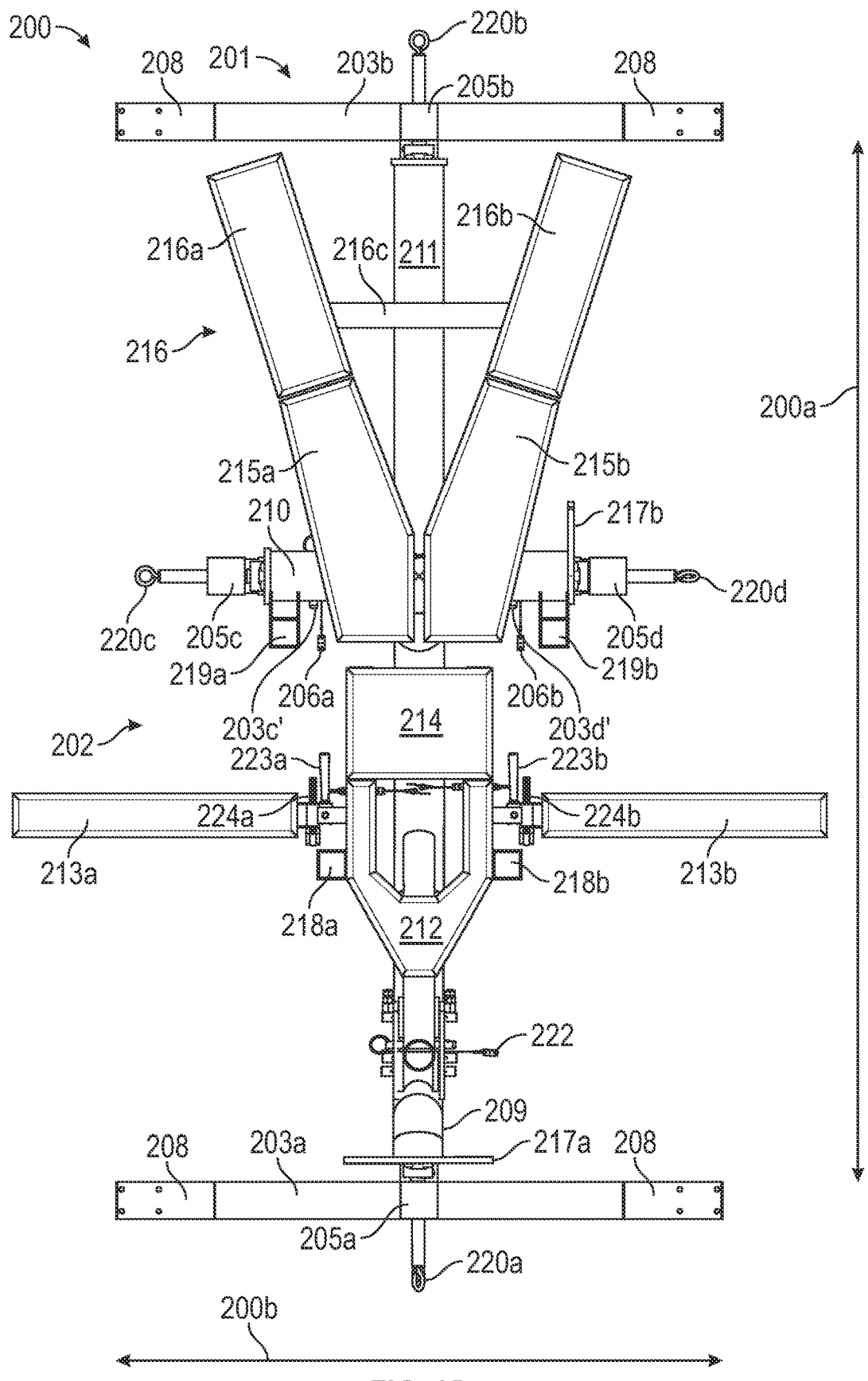
FIG. 2B is a top view of an embodiment of an apparatus for patient positioning and repositioning.
Figure 2C:
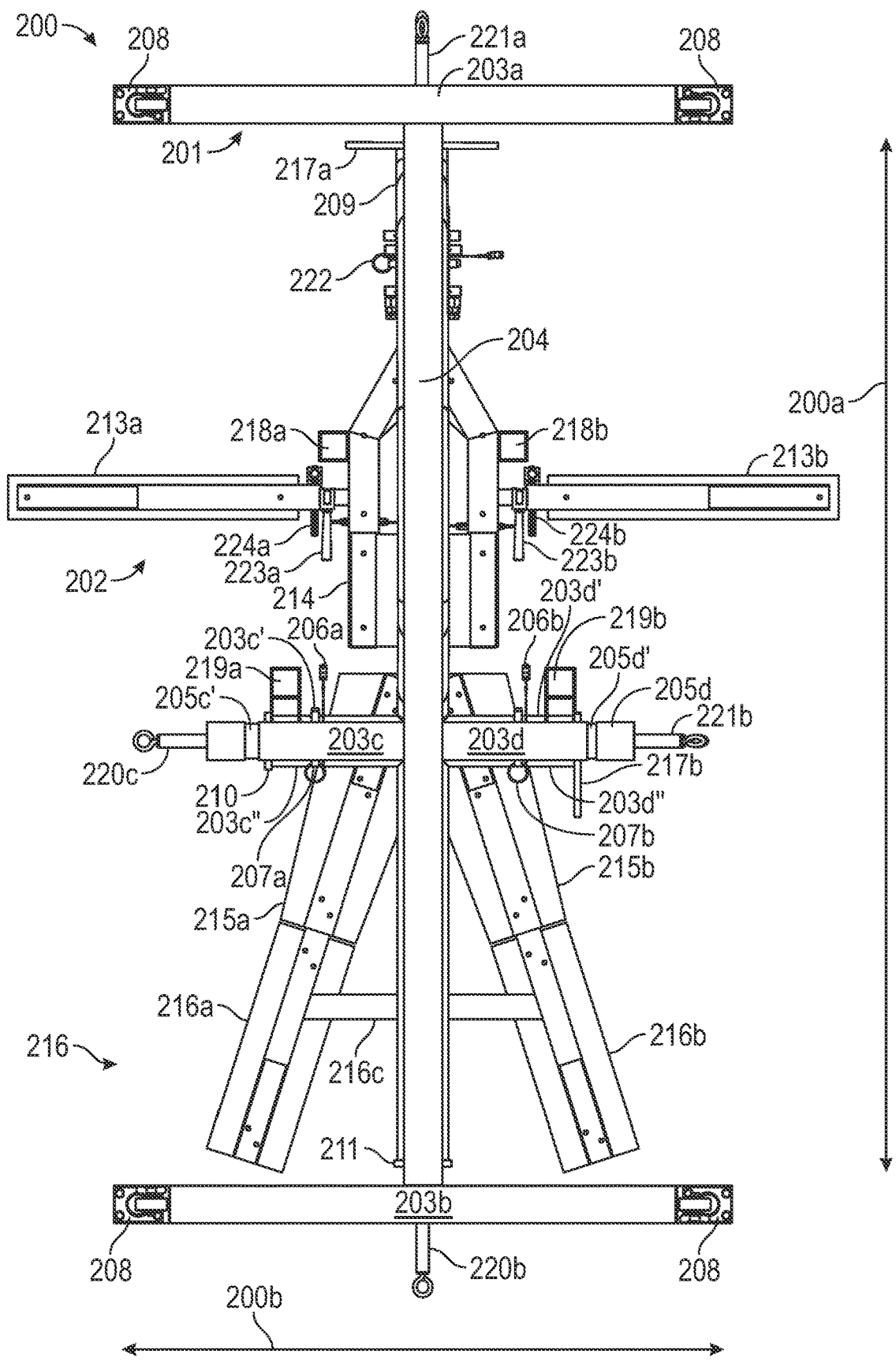
FIG. 2C is a bottom view of an embodiment of an apparatus for patient positioning and repositioning.

FIGS. 2B and 2C are top and bottom views, respectively, of apparatus 200. Left arm pad 213a is adjustably-attached to head pad 212 via left coronal cam lock 223a and left axial cam lock 224a. Right arm pad 213b is adjustably-attached to head pad 212 via right coronal cam lock 223b and right axial cam lock 224b.

Figure 2D:
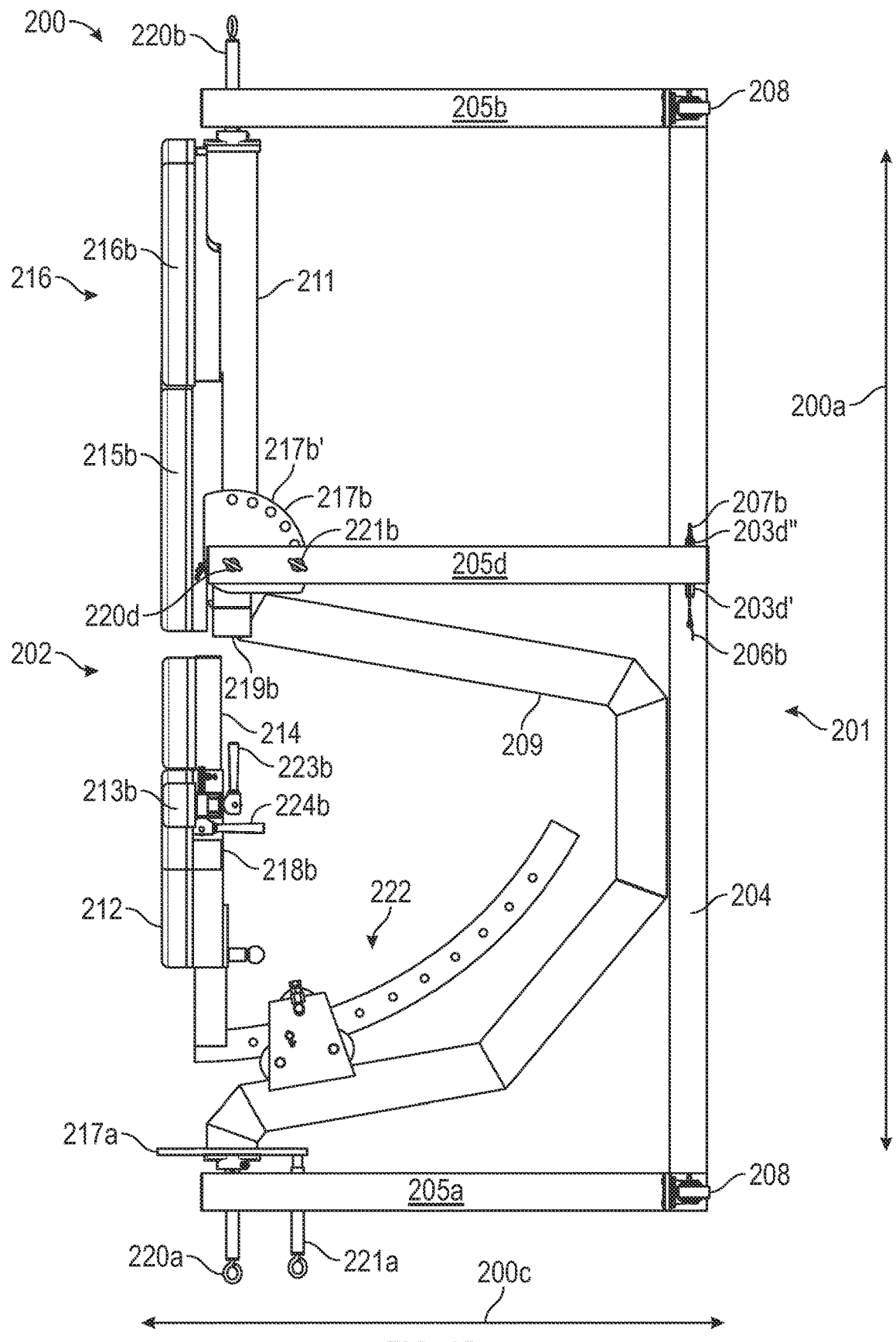
FIG. 2D is a right side view of an embodiment of an apparatus for patient positioning and repositioning.

Turning to FIG. 2D, a right side view of apparatus 200 is shown. In apparatus 200, hip tube 210 (not seen in FIG. 2D) further comprises pitch member 217b at its lateral axis right end, wherein pitch member 217b further comprises holes 217b'.

Figure 2E:
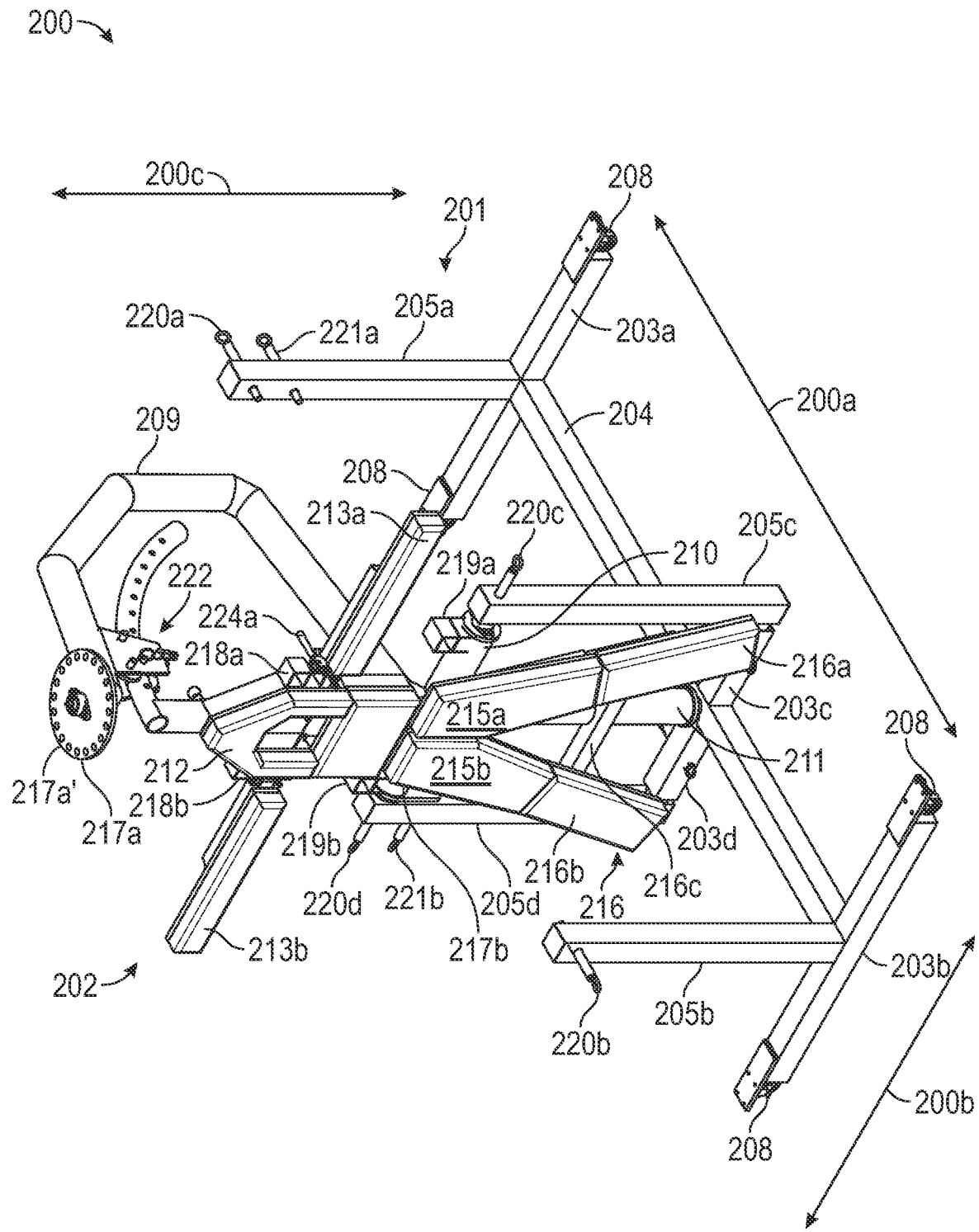
FIG. 2E is an orthogonal view of an embodiment of an apparatus for patient positioning and repositioning.

FIG. 2E illustrates the ability of apparatus 200 to position a patient in a vertical position. Compared to earlier FIGS. 2B-2D, hip tube 210 is rotated such that gimbal assembly 202 pivots about lateral axis 200b 90 degrees (referred to as modifying "pitch" in the "sagittal" plane). The degree of pitch is controlled by flexion pin 221b, which engages holes 217b' of pitch member 217b. Apparatus 200 allows for a pitch range of approximately 90 degrees, with FIG. 2E showing maximum pitch and FIG. 2A illustrating minimum pitch. In other embodiments of the invention, roll pitch range can exceed 90 degrees. When gimbal assembly 202 is at a pitch other than 0 degrees, head tube 209 is detached from head support 205a and foot tube 211 is detached from foot support 205b. While pitch member 217b of apparatus 200 is located at the right end of the apparatus, certain other embodiments of the invention may contain a pitch member on the left end of the apparatus or both at the right end and the left end of the apparatus.

Figure 2F:
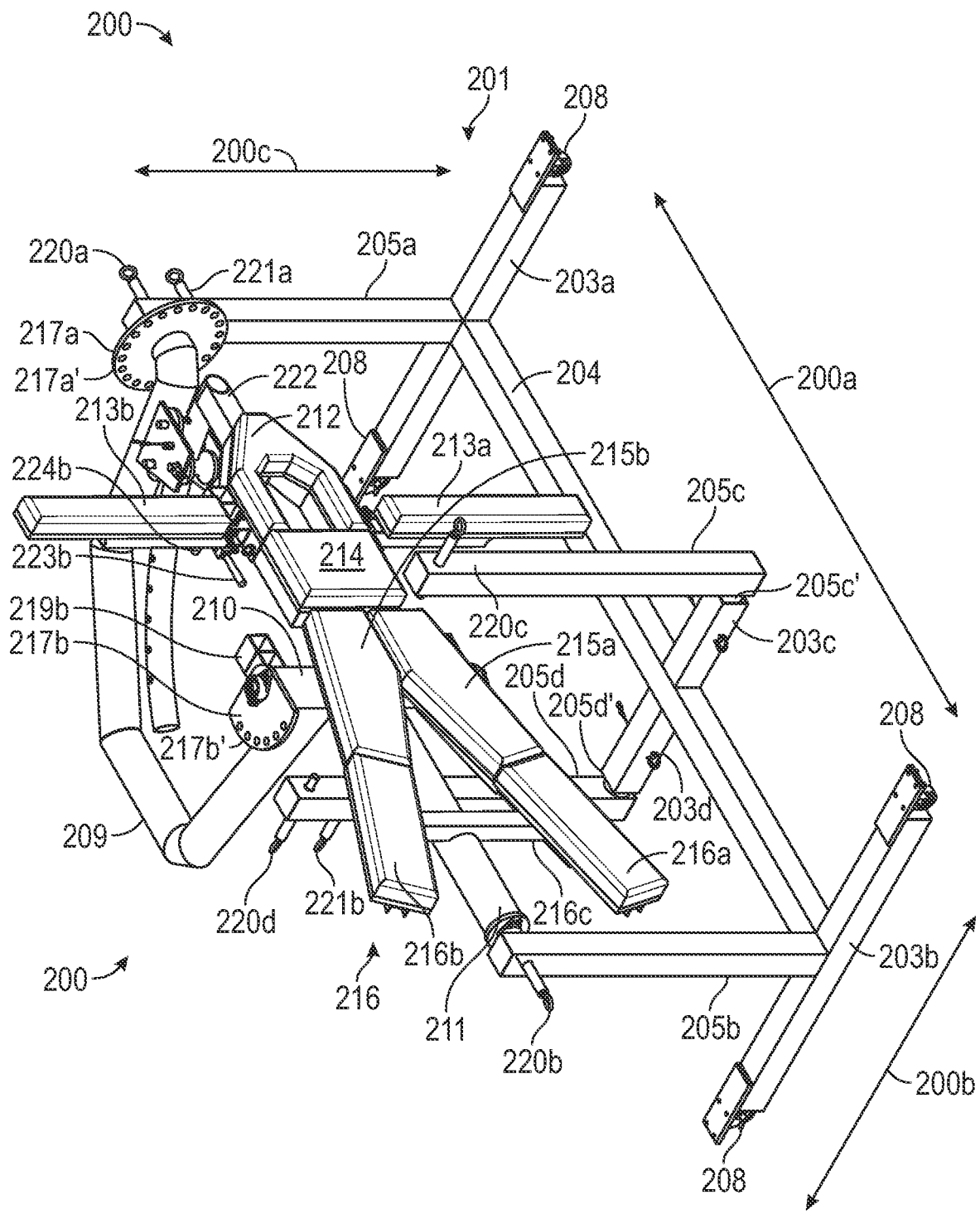
FIG. 2F is an orthogonal view of an embodiment of an apparatus for patient positioning and repositioning illustrating a lateral positioning configuration.
Figure 2G:
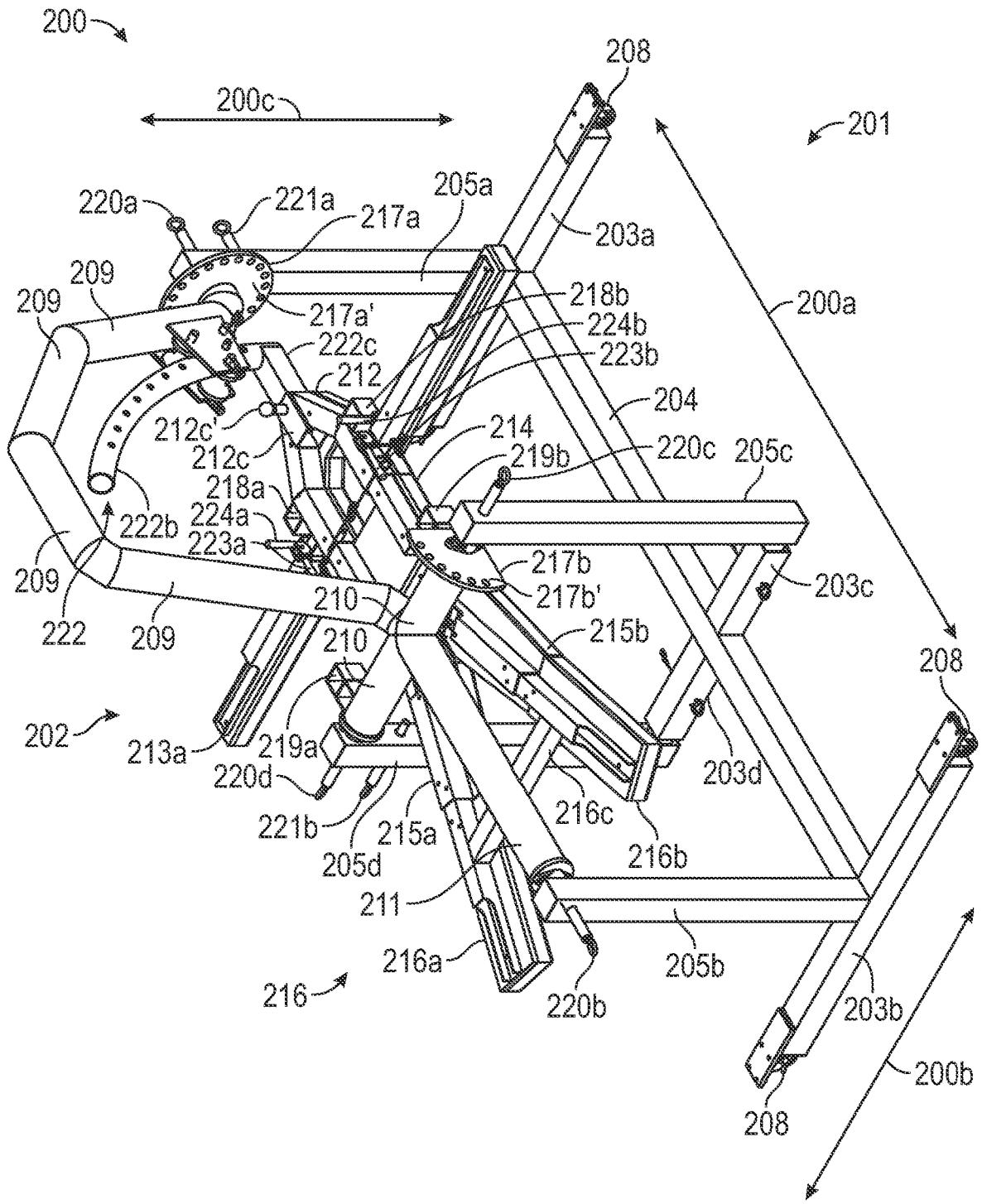
FIG. 2G is an orthogonal view of an embodiment of an apparatus for patient positioning and repositioning illustrating a prone positioning configuration.

FIGS. 2F and 2G illustrate the ability of apparatus 200 to position a patient in lateral and prone configurations, respectively. Head tube 209 is articulated such that gimbal assembly 202 is pivoted about the longitudinal axis 200a (referred to as "roll" in the "axial" plane). The degree of roll is controlled by roll pin 221a by engaging holes 217a' of roll member 217a. Apparatus 200 allows for a roll range of 360 degrees, with FIGS. 2F and 2G showing intermediate roll and FIG. 2A showing minimum roll. When gimbal assembly 202 is at a roll other than 0 degrees or an integer multiple of 180 degrees, hip tube 210 is detached from hip supports 205c, 205d. While roll member 217a of apparatus 200 is located at the head, certain other embodiments of the invention may contain a roll member at the foot of the apparatus or both at the head and the foot of the apparatus.

FIG. 2G illustrates a configuration where the roll in the axial plane is 180 degrees and the removable attachment point of head pad 212 to head tube 209 via flexion assembly 222. Head pad 212 comprises lumbar receivers 212a, 212b (not seen in FIG. 2G) and slide receiver 212c, which further comprises knob 212c'. Flexion assembly 222 comprises flexion-attachment member 222a, flexion tube 222b, and slide inserter 222c. Flexion assembly 222 allows head pad 212 to translate along the longitudinal axis of head tube 209, herein referred to as "slide." The degree of slide is controlled by knob 212c' engaging slide inserter 222c while slide inserter 222c is inserted into slide receiver 212c at varying points of overlap.

Figure 2H:
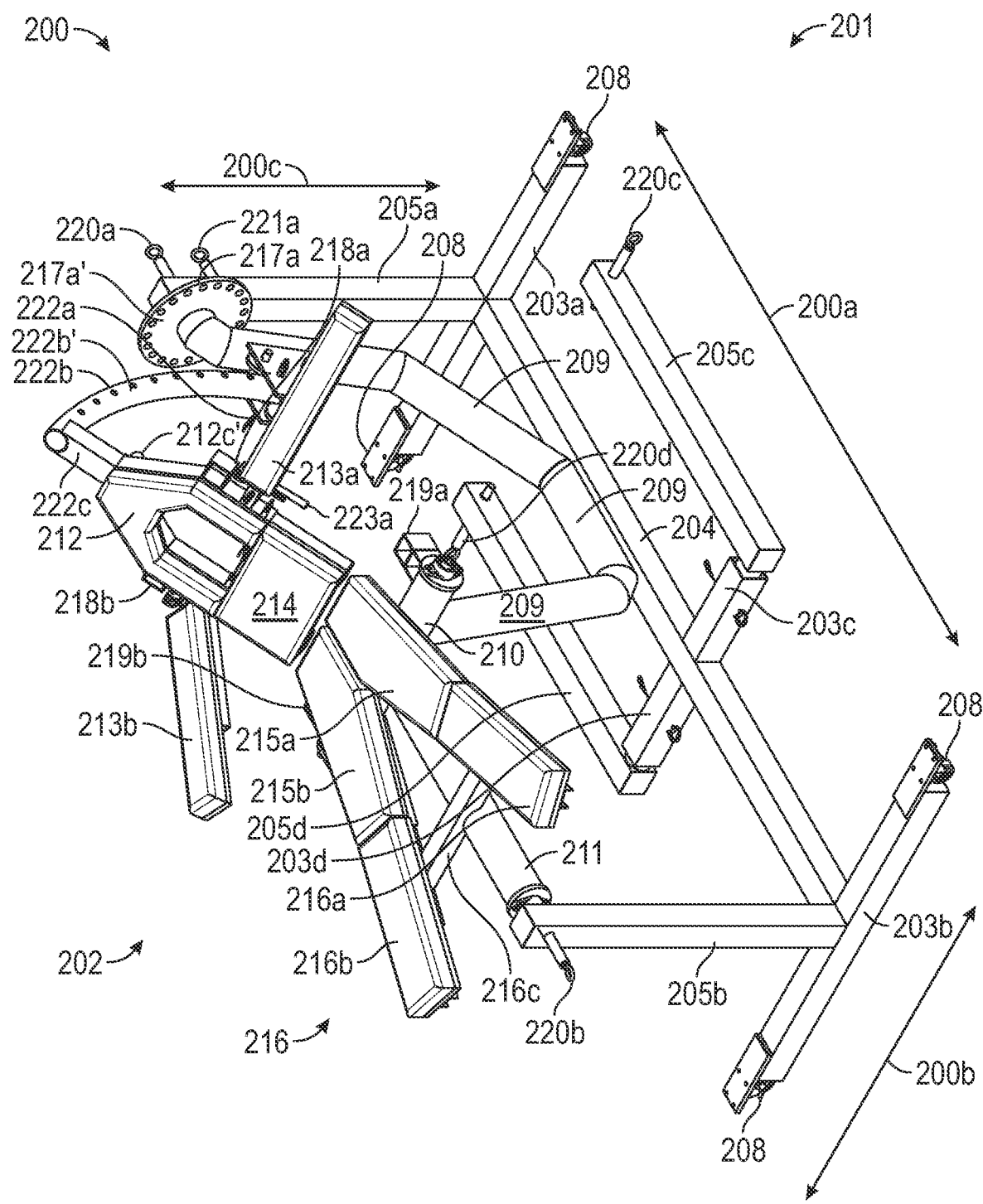
FIG. 2H is an orthogonal view of an embodiment of an apparatus for patient positioning and repositioning illustrating a seated positioning configuration.

FIG. 2H illustrates the ability of apparatus 200 to position a patient in a semi-recumbent seated configuration with one extended arm position. Flexion tube 222b comprises holes 222b' adapted to receive flexion pin 221b. Flexion assembly 222 allows head pad 212 to translate in a curved path relative to head tube 209, herein referred to as "flex." The degree of flex is controlled by flexion pin 221b engaging holes 222b' of flexion tube 222b. Apparatus 200 allows for a flex range of approximately 45 degrees, with FIG. 2H showing maximum flex and FIG. 2A showing minimum flex. In other embodiments of the invention, roll range can exceed 45 degrees.

FIG. 2H also illustrates the variable positioning of arm pads 213a, 213b relative to head pad 212. Left coronal cam lock 223a allows left arm pad 213a to pivot, at the articulation point of left arm pad 213a with head pad 212, about the vertical axis of head pad 212, in the plane of the longitudinal axis of head pad 212 by the lateral axis of head pad 212 (referred to as "yaw" in a "coronal" plane). Apparatus 200 allows for a yaw range of approximately 110 degrees, with FIG. 2H showing neutral yaw of left arm pad 213a. Left arm pad 213a is operable of approximately 20 degrees of head-ward yaw wherein the lateral axis left end of left arm pad 213a translates in a coronal plane towards head pad 212. Left arm pad 213a is operable of approximately 90 degrees of foot-ward yaw wherein the lateral axis left end of left arm pad 213a translates in a coronal plane towards left thigh pad 215a. The variable attachment of right arm 213b is similarly capable of yaw via right coronal cam lock 223b (not seen in FIG. 2H). Left axial cam lock 224a allows left arm pad 213a to pivot, at the articulation point of left arm pad 213a with head pad 212, about the longitudinal axis of head pad 212, in the plane of the lateral axis of head pad 212 by the vertical axis of head pad 212 (referred to as "adduction"). The variable attachment of right arm 213b is similarly capable of adduction via right coronal cam lock 223b (not seen in FIG. 2H). Apparatus 200 allows for an adduction range of approximately 100 degrees, with FIG. 2H showing maximum adduction of right arm pad 213b and minimum adduction of left arm pad 213a.

The term "cam lock" is a device known to those of ordinary skill in the art. Other variable attachment mechanisms resulting in similar yaw and adduction will be readily apparent to those of ordinary skill in the art.

Additionally, FIG. 2H illustrates the adjustable attachment of hip supports 205c, 205d to hip bases 203c, 203d, respectively. In FIG. 2H, hip supports 205c, 205d have been pivoted, in the sagittal plane, from their respective articulations with hip bases 203c and 203d, and about the lateral axes of hip bases 203c and 203d, respectively, such that hip supports 205c and 205d now rest on the floor oriented in longitudinal axis 200a. This minimizes the hindrance hip supports 205c and 205d might have on one or more healthcare providers accessing gimbal assembly 202.

Figure 2I:
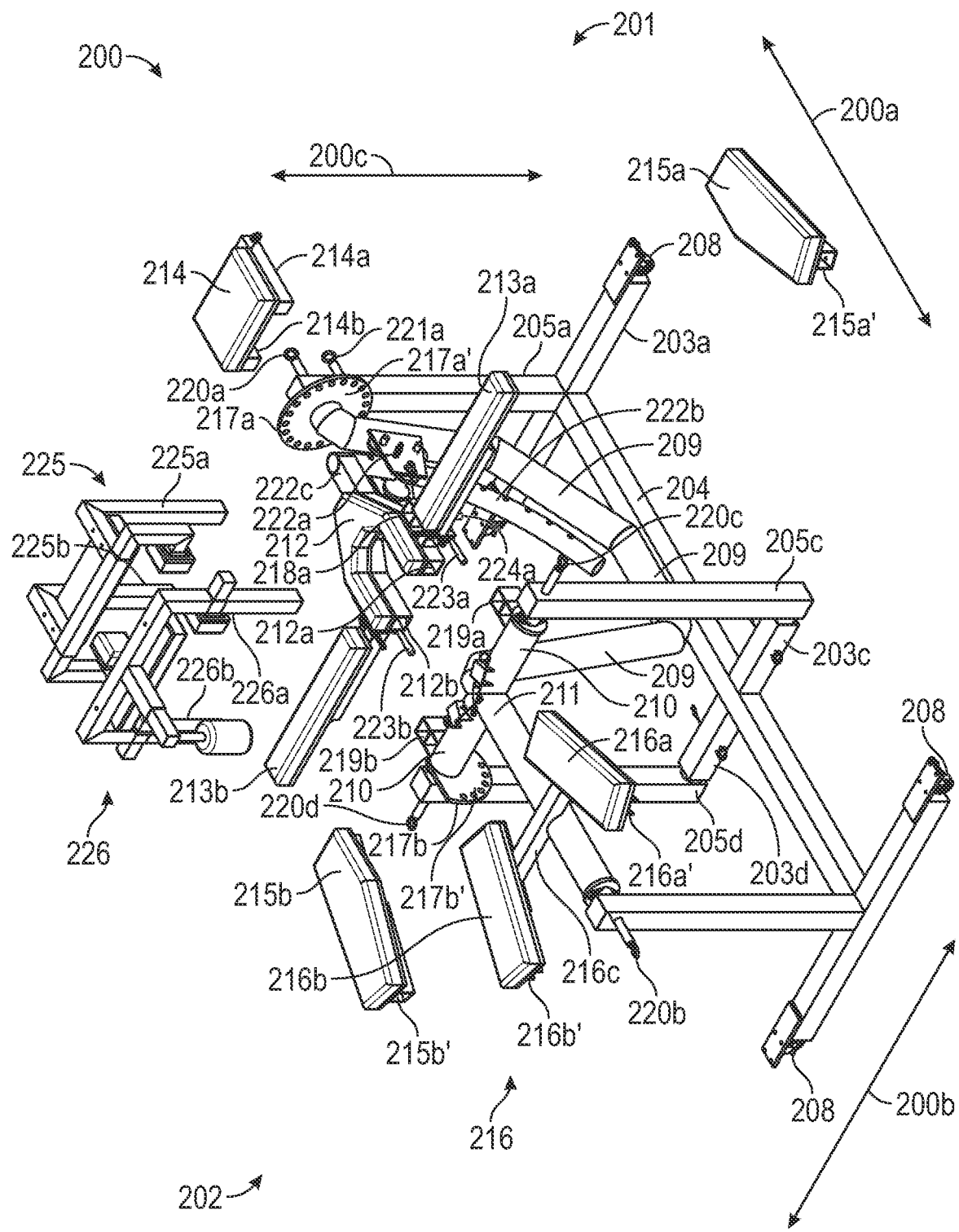
FIG. 2I is an exploded view of an embodiment of an apparatus for patient positioning and repositioning.
Figure 2J:
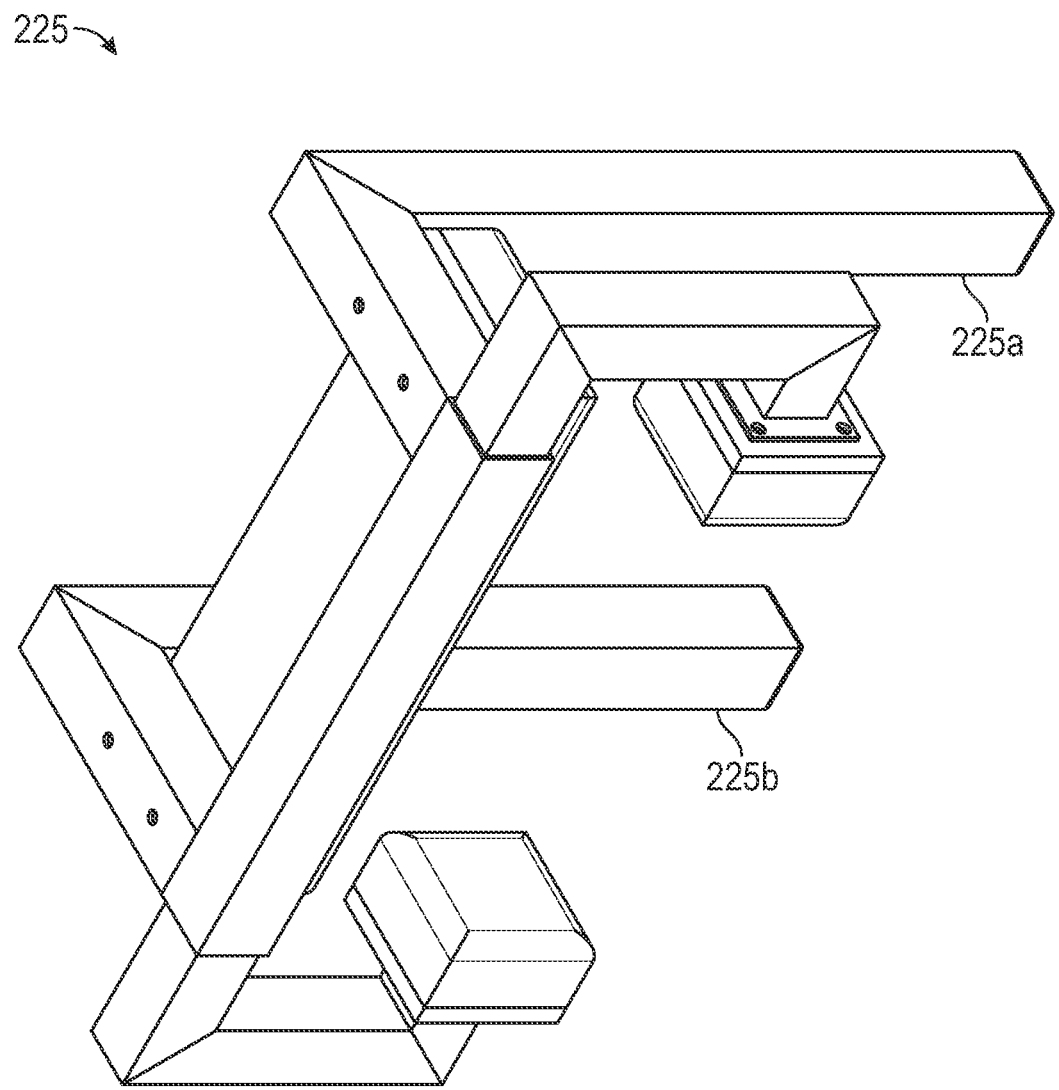
FIG. 2J is an orthogonal view of a shoulder cage component of an embodiment of an apparatus for patient positioning and repositioning in accordance with the present invention.

FIG. 2I shows an exploded view of apparatus 200. Apparatus 200 further comprises shoulder cage 225 and hip cage 226. Shoulder cage 225, comprises shoulder cage inserters 225a and 225b (shown in detail in FIG. 2G), and adjustably-attaches to head pad 212 via shoulder cage inserters 225a and 225b inserting into shoulder cage receivers 218a and 218b, respectively. Similarly, hip cage 226, which comprises hip cage inserters 226a and 226b (shown in detail in FIG.

2K), adjustably-attaches to hip tube 210 via hip cage inserters 226a and 226b inserting into hip cage receivers 219a and 219b, respectively.

Head pad 212 further comprises lumbar receivers 212a and 212b and lumbar pad 214 further comprises lumbar inserters 214a and 214b, wherein lumbar pad 214 adjustably-attaches to head pad 212 via lumbar inserters 214a and 214b inserting into lumbar receivers 212a and 212b, respectively. Left thigh pad 215a further comprises left thigh inserter 215a' and left foot pad 216a further comprises left thigh receiver 216a', wherein left thigh pad 215a adjustably-attaches to left foot pad 216a via left thigh inserter 215a' inserting into left thigh receiver 216a'. Right thigh pad 215b further comprises right thigh inserter 215b' and right foot pad 216b further comprises right thigh receiver 216b' wherein right thigh pad 215b adjustably-attaches to right foot pad 216b via right thigh inserter 215b' inserting into right thigh receiver 216b'. Securement between shoulder cage inserters 225a and 225b and shoulder cage receivers 218a and 218b, hip cage inserters 226a and 226b and hip cage receiver 219a and 219b, lumbar inserters 214a and 214b and lumbar receivers 212a and 212b, and thigh inserters 215a' and 215b' and thigh receivers 216a' and 216b' can be via any securement means known to one of skill in the art, including but not limited to pins, nuts and bolts. Other securement means will be readily apparent to those of ordinary skill in the art.

For all the various inserter and receiver mechanisms described herein, further embodiments are contemplated wherein said inserter and receiver mechanisms comprise one or more inserters and one or more receivers, respectively.

Figure 2K:
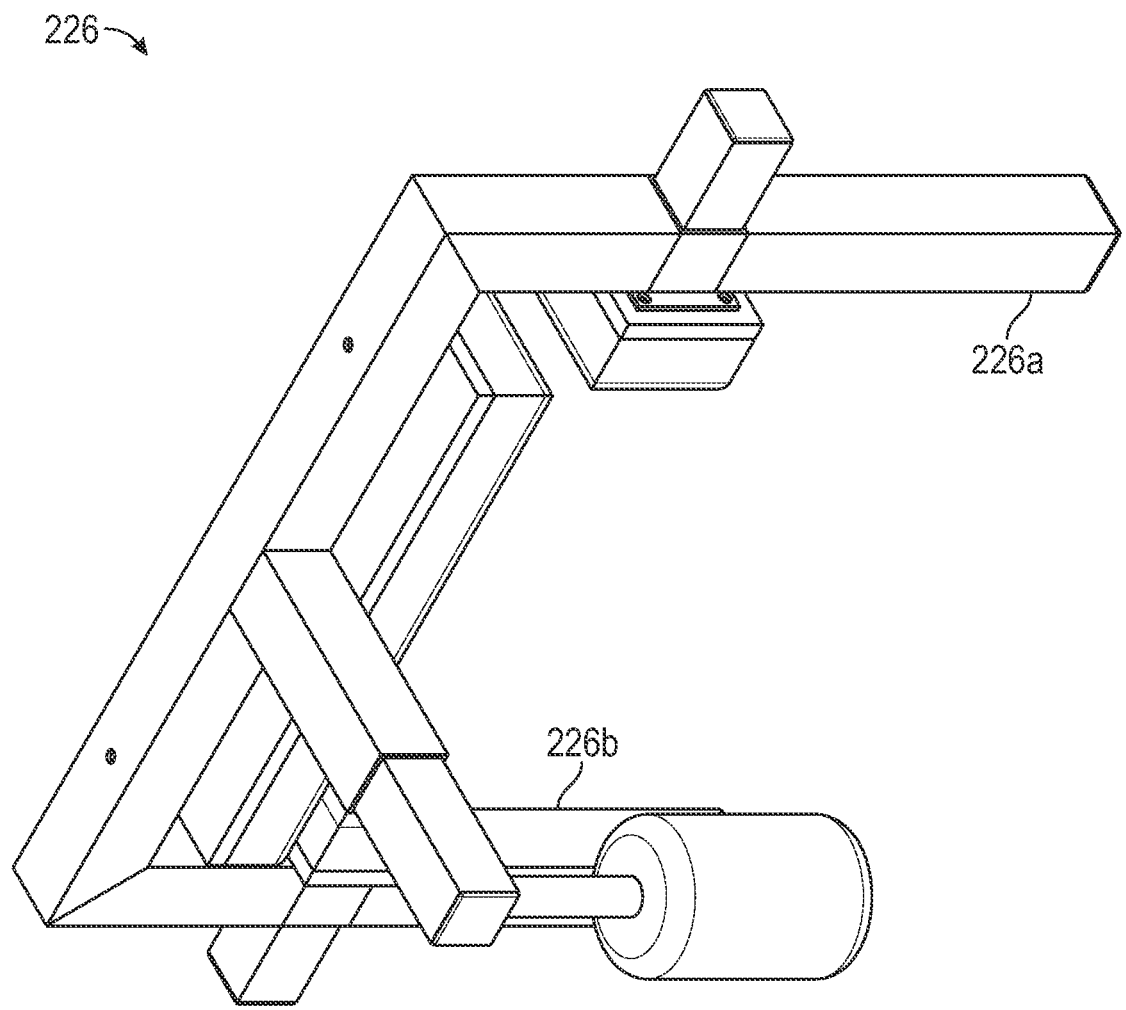
FIG. 2K is an orthogonal view of a hip cage component of an embodiment of an apparatus for patient positioning and repositioning in accordance with the present invention.

Apparatuses disclosed herein are designed to accommodate an occupant and allow users to selectively maneuver and position the patient. The occupant can be human or non-human. The occupant can be restrained upon the apparatus shown in FIGS. 1-2K via cage mechanisms (e.g., shoulder cage 225 and hip cage 226 disclosed herein) or retaining pads, cushions, slings, straps, belts, harnesses, ribbons, sashes, cinctures, bands, tacks, girdles, and the like. Other restraining means will be readily apparent to those of ordinary skill in the art.

The apparatuses disclosed herein allows users to selectively position and reposition an occupant. Among other things, such positioning and repositioning can be done during a procedure and can be done without interfering with the sterility of an operating field. Users can direct positioning and repositioning via direct, manual, automated, or remote means. In certain embodiments, the apparatuses disclosed herein may further comprise screw-driven, cable-driven and piston-driven drives, power sources, motors, drives, pulleys, controls, remote controls, computers, sensors, programs, codes, automations, etc. to facilitate the various positioning features disclosed herein (e.g., roll, pitch, flex, yaw, adduction, and slide), and in particular, effect rotational movement on tubes/shafts as would be understood by one of skill in the art.

The various positioning features disclosed herein allow customizable adjustment of the apparatuses disclosed herein to suit a given occupant. In certain embodiments, apparatus 200 is sized to accommodate a 99th percentile male and adjustable to accommodate a 1st percentile female. In certain embodiments, apparatus 200 has an overall size of approximately 90 inches in length by 40 inches in width by 44 inches in height. In certain embodiments, primary components of apparatus 200 are sized to accommodate a 400lb load at beam center.

The apparatus components disclosed herein may each comprise carbon, carbon fiber, carbon fiber composite, aluminum, titanium, metal, plastic, fiber, wood, textile, polymer, silicone, latex, polyurethane, polyester, cloth, sponge, lead, glass, polymethyl methacrylate, clinical agent, or material that is rigid or flexible, thermally or electromagnetically conducting or insulating or reflective, coated (wherein such coating may be clinical agent) or non-coated, textured or non-textured, ablating or non-ablating, radioactive or non-radioactive, radiopaque or radiolucent, etc., or a combination thereof.

In some embodiments, the apparatuses disclosed herein are adapted to allow procedures in conjunction with guidance from imaging technologies, including but not limited to portable or non-portable radiography ("x ray" or "x-ray"), computed tomography ("CT"), ultrasound, magnetic resonance imaging ("MRI"), positron emission tomography ("PET"), or nuclear medicine imaging.

Also disclosed herein are methods of apparatus positioning. In certain embodiments, a method of apparatus positioning pertains to an apparatus comprising a frame and a gimbal, wherein the gimbal is adjustably-attached to the frame at two or more attachment points, the gimbal is operable of rotation about two or more axes relative to the frame, one axis of rotation contains one or more of the attachment points, and each of the other one or more axes of rotation contain one or more of the other attachment points. The method comprises the steps of selecting a desired axis of rotation, selectively attaching the gimbal to the frame at the one or more attachment points in the axis of desired rotation, selectively detaching the gimbal from the frame at the one or more attachment points not in the axis of desired rotation, and selectively rotating the gimbal relative to the frame about the desired axis of rotation.

In certain embodiments, a method of apparatus positioning is performed using apparatus 200. In some embodiments, the desired axis of rotation is about longitudinal axis 200a. Thus, the selected points of attachment comprise the vertical axis top of head support 205a and the vertical axis top of foot support 205b, and the selected points of detachment comprise the vertical axis tops of hip supports 205c and 205d. In further embodiments, the method can further comprise pivoting hip supports 205c and 205d at their respective articulations with hip bases 203c and 203d about lateral axis 200b. In other further embodiments, the method can further comprise detaching hip supports 205c and 205d from hip bases 203c and 203d. In some embodiments, the desired axis of rotation is about lateral axis 200b. Thus, the selected points of attachment comprise the tops of hip supports 205c and 205d, and the selected points of detachment comprise the tops of head support 205a and foot support 205b.

Any and all materials, shapes, and dimensions, and any and all minimums, maximums, and ranges contained herein are for illustrative and exemplary purposes only and are not intended to be limiting.

Any and all figures, drawings, illustrations, and depictions, and any and all descriptions contained herein are for illustrative and exemplary purposes only. They are not intended to be exact nor to scale.

Contemplated applications for all embodiments of apparatuses and methods disclosed herein include commercial, private, governmental, educational, research, healthcare, pharmaceutical, dental, medical, cosmetic, chiropractic, massage, veterinary, environmental, charitable, recreational, entertainment, touristic, travel, and other applications.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

What is claimed is:

1. A patient positioning apparatus, comprising:
    a longitudinal axis, a lateral axis, and a vertical axis, each perpendicular to each other;
    a base frame assembly operable to support a patient, comprising:
        a longitudinal base bar, wherein the longitudinal base bar extends along the longitudinal axis and is located approximately at a bottom of the vertical axis;
        a head base, wherein the head base extends along the lateral axis and is located approximately at a first end of the longitudinal axis and the bottom of the vertical axis;
        a foot base, wherein the foot base extends along the lateral axis and is located approximately at a second end of the longitudinal axis opposite the first end of the longitudinal axis and the bottom of the vertical axis;
        a left hip base, wherein the left hip base extends along the lateral axis and is located approximately at the bottom of the vertical axis and between the first end and the second ends of the longitudinal axis;
        a right hip base, wherein the right hip base extends along the lateral axis and is located approximately at the bottom of the vertical axis and between the first end and the second end of the longitudinal axis;
        a head support, wherein the head support extends along the vertical axis and is located approximately at the first end of the longitudinal axis;
        a foot support, wherein the foot support extends along the vertical axis and is located approximately at the second end of the longitudinal axis;
        a left hip support, wherein the left hip support extends along the vertical axis and is located between the first and the second ends of the longitudinal axis; and
        a right hip support, wherein the right hip support extends along the vertical axis and is located a between the first and the second ends of the longitudinal axis; and
    a gimbal, comprising:
        a head tube, further comprising a head tube head and a head tube foot, wherein the head tube head further comprises a roll member;
        a head pad;
        a hip tube, further comprising a hip tube left and a hip tube right, wherein the hip tube right further comprises a pitch member;
        a foot tube, further comprising a foot tube head and a foot tube foot; and
        a foot assembly; and
    wherein:
        the head tube head is attached to the head support;
        the foot tube foot is attached to the foot support;
        the hip tube left is attached to the left hip support;
        the hip tube right is attached to the right hip support;
        the gimbal is rotatable about the longitudinal axis;
        the roll member is operable to control the gimbal's rotation about the longitudinal axis;
        the gimbal is rotatable about the lateral axis;
        the pitch member is operable to control the gimbal rotation about the lateral axis.

2. The patient positioning apparatus of claim 1, wherein the patient positioning apparatus further comprises a roll pin.

3. The patient positioning apparatus of claim 1, wherein the patient positioning apparatus further comprises a flexion pin.

4. The patient positioning apparatus of claim 1, wherein the gimbal is operable to rotating a patient about the longitudinal axis in the range of about 0 to 360 degrees.

5. The patient positioning apparatus of claim 1, wherein the gimbal is operable of rotating a patient about the lateral axis in the range of about 0 to 90 degrees.

6. The patient positioning apparatus of claim 1, wherein the base frame assembly further comprises a wheel assembly.

7. The patient positioning apparatus of claim 1, wherein the gimbal further comprises a flexion assembly that attaches the head pad and the head tube and is operable to control linear translation of the head pad relative to the head tube.

8. The patient positioning apparatus of claim 7, wherein the head pad further comprises a slide receiver and a knob.

9. The patient positioning apparatus of claim 8, wherein the flexion assembly further comprises a slide inserter and is operable to control linear translation of the head pad relative to the head tube via the knob, and wherein the knob is operable to engage the slide inserter while the slide inserter is inserted through the slide receiver.

10. The patient positioning apparatus of claim 7, further comprising a flexion pin, and the flexion assembly further comprising one or more holes.

11. The patient positioning apparatus of claim 1, wherein the gimbal further comprises a left coronal cam lock that controls left arm pad rotation relative to the gimbal.

12. The patient positioning apparatus of claim 1, wherein the gimbal further comprises a right coronal cam lock controls right arm pad rotation relative to the gimbal.

13. The patient positioning apparatus of claim 1, further comprising a shoulder cage adapted to support an occupant.

14. The patient positioning apparatus of claim 13, wherein the shoulder cage further comprises a left shoulder cage inserter and a right shoulder cage inserter.

15. The patient positioning apparatus of claim 1, further comprising a hip cage adapted to support an occupant.

16. The patient positioning apparatus of claim 15, wherein the hip cage further comprises a left hip cage receiver and a right hip cage receiver.

17. The patient positioning apparatus of claim 1, further comprising one or more restraining means adapted to restrain an occupant.

18. The patient positioning apparatus of claim 17, wherein the one or more restraining means are selected from the group consisting of pads, cushions, slings, straps, belts, harnesses, ribbons, sashes, cinctures, bands, tacks, and girdles.

19. The patient positioning apparatus of claim 1, further comprising a control means selected from the group consisting of motors, drives, pulleys and cables.

20. The patient positioning apparatus of claim 1, wherein the base frame assembly comprises one or more materials selected from the group consisting of carbon, carbon fiber, aluminum, titanium, metal, plastic, fiber, wood, textile, polymer, silicone, latex, polyurethane, polyester, cloth, sponge, lead, glass, polymethyl methacrylate, or clinical agent.

21. The patient positioning apparatus of claim 1, further comprising one or more pads.

22. The patient positioning apparatus of claim 1, further comprising a plurality of limb receivers.

23. A method of patient positioning on an apparatus comprising a frame and a gimbal, wherein the gimbal is attached to the frame at two or more attachment points, the gimbal is operable of rotation about two or more axes relative to the frame, one axis of rotation contains one or more of the attachment points, and each of the other one or more axes of rotation contain one or more of the other attachment points, comprising the steps of:
    selecting a desired axis of rotation;
    detaching the gimbal from the frame at the one or more attachment points not in the axis of desired rotation;
    rotating the gimbal relative to the frame about the desired axis of rotation; and
    attaching the gimbal to the frame at the one or more attachment points in the axis of desired rotation.

\* \* \* \* \*